US008809593B2

(12) United States Patent
Rode et al.

(10) Patent No.: US 8,809,593 B2
(45) Date of Patent: Aug. 19, 2014

(54) PROCESS FOR PREPARATION OF HYDROXYACETONE OR PROPYLENE GLYCOL

(75) Inventors: Chandrasshekhar Vasant Rode, Maharashtra (IN); Amol Mahalingappa Hengne, Maharashtra (IN); Ajay Ashok Ghalwadkar, Maharashtra (IN); Rasika Bharat Mane, Maharashtra (IN); Pravinkumar Hansraj Mohite, Maharashtra (IN); Hari Shankar Potdar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 65 days.

(21) Appl. No.: 13/578,698

(22) PCT Filed: Feb. 25, 2011

(86) PCT No.: PCT/IB2011/000395
§ 371 (c)(1),
(2), (4) Date: Nov. 9, 2012

(87) PCT Pub. No.: WO2011/138643
PCT Pub. Date: Nov. 10, 2011

(65) Prior Publication Data
US 2013/0079561 A1  Mar. 28, 2013

(30) Foreign Application Priority Data
Feb. 26, 2010  (IN) .............. 436/DEL/2010

(51) Int. Cl.
| | | |
|---|---|---|
| C07C 45/52 | (2006.01) |
| C07C 29/60 | (2006.01) |
| B01J 37/18 | (2006.01) |
| B01J 35/10 | (2006.01) |
| B01J 23/86 | (2006.01) |
| B01J 23/72 | (2006.01) |
| B01J 37/03 | (2006.01) |
| B01J 35/00 | (2006.01) |
| B01J 29/76 | (2006.01) |
| C07C 45/29 | (2006.01) |
| C07C 29/145 | (2006.01) |
| C07C 45/00 | (2006.01) |
| B01J 23/00 | (2006.01) |
| B01J 21/08 | (2006.01) |
| B01J 21/04 | (2006.01) |
| B01J 21/18 | (2006.01) |

(52) U.S. Cl.
CPC ............. *C07C 45/52* (2013.01); *B01J 37/18* (2013.01); *B01J 21/08* (2013.01); *B01J 21/04* (2013.01); *B01J 35/1019* (2013.01); *B01J 23/868* (2013.01); *B01J 2523/00* (2013.01); *B01J 23/72* (2013.01); *B01J 35/1023* (2013.01); *B01J 37/035* (2013.01); *B01J 35/002* (2013.01); *B01J 29/7615* (2013.01); *B01J 21/18* (2013.01); *B01J 35/006* (2013.01); *C07C 45/292* (2013.01); *B01J 35/1014* (2013.01); *C07C 29/145* (2013.01); *C07C 45/00* (2013.01); *C07C 29/60* (2013.01); *B01J 37/031* (2013.01); *B01J 23/002* (2013.01)
USPC .......................................... 568/405; 568/861

(58) Field of Classification Search
USPC .................................................... 568/405, 861
See application file for complete search history.

(56) References Cited
U.S. PATENT DOCUMENTS
2010/0312024 A1   12/2010   Henkelmann et al.

FOREIGN PATENT DOCUMENTS
WO   WO 2009/027502 A2   3/2009

OTHER PUBLICATIONS
International Search Report PCT/IB2011/000395 dated Feb. 6, 2012.
International Preliminary Report on Patentability PCT/IB2011/000395 dated Sep. 7, 2012.
Rasika B. Mane et al., "Cu:Al Nano Catalyst for Selective Hydrogenolysis of Glycerol to 1,2-Propanediol", Catal. Lett. (2010) 135: 141-147.
R.B. Mane et al., "Role of promoters in copper chromite catalysts for hydrogenolysis of glycerol", Catalysis Today 164 (2011) 447-450.

*Primary Examiner* — Sikarl Witherspoon
(74) *Attorney, Agent, or Firm* — Foley & Lardner LLP

(57) ABSTRACT

The present invention relates to a process for the preparation of the hydroxyacetone or 1,2 propylene glycol. More particularly, the present invention relates to a process for preparation of hydroxyacetone or 1,2 propylene glycol by glycerol. Further, the said process is catalyzed by metal catalysts that results in 80 to 100% selectivity towards conversion of glycerol to hydroxyacetone (acetol) or 1,2 propylene glycol (1,2 PG).

21 Claims, 4 Drawing Sheets

PROCESS FOR PREPARATION OF HYDROXYACETONE OR PROPYLENE GLYCOL

CROSS-REFERENCE TO RELATED APPLICATIONS

This application is the U.S. National Phase of PCT/IB2011/000395 dated Feb. 25, 2011, which claims priority from India Application No. 436/DEL/210 filed Feb. 26, 2010. The entirety of each is incorporated herein by reference in entirety.

FIELD OF THE INVENTION

The present invention relates to a process for the preparation of the hydroxyacetone or propylene glycol. More particularly, the present invention relates to a process for preparation of hydroxyacetone or 1,2 propylene glycol by glycerol. Further, the said process is catalyzed by metal catalysts that results in 80 to 100% selectivity towards conversion of glycerol to hydroxyacetone (acetol) or 1,2 propylene glycol (1,2 PG).

BACKGROUND AND PRIOR ART OF THE INVENTION

It is known that hydrogenolysis of glycerol involves first dehydration to give acetol followed by its hydrogenation to 1,2-propylene glycol (1,2-PG). In direct hydrogenation route, these steps are carried out together, however, dehydration step does not require hydrogen and also the kinetics of both these steps being different and several side products are formed. This is a major drawback of the single step hydrogenation route.

WO/2005/095536 titled "Method of producing lower alcohols from glycerol" and the thesis titled "Catalytic conversion of glycerol and sugar alcohols to value-added products" by Mohanprasad A. Dasari, chapter 4 titled "Dehydration of glycerol, to acetol via catalytic reactive distillation" discloses preparation of relatively pure hydroxyacetone from glycerol employing metallic catalysts including copper, nickel, alumina and others in the presence of water, but the selectivity of the process to hydroxyacetone is only up to 65%.

In the article "Vapor-phase reaction of polyols over copper catalysts" by Masaki Akiyama, Ryoji Takahashi, Takayoshi Hara, Kanichiro Inui and Masahiro Yokota describe the vapor-phase reaction of triols and diols over copper metal catalysts. Triols, such as 1,2,3-propanetriol (glycerol) and 1,2,3- and 1,2,4-butanetriols, are dehydrated to corresponding hydroxyketones, while 1,2-propyleneglycol is dehydrogenated to form hydroxyacetone. Supported copper as well as pure copper metal was an effective catalyst for the dehydration of glycerol to produce hydroxyacetone under inert conditions. Alumina-supported copper showed the highest catalytic activity with hydroxyacetone selectivity of >90 mol % at ambient pressure of nitrogen and at 250° C.

From prior art search results, it is clear that liquid phase selective dehydration of glycerol to hydroxyacetone resulting in 100% selectivity towards hydroxyacetone has not been successfully attempted so far. Further, dehydration of glycerol in presence of water to attain 100% selectivity to hydroxyacetone by the selective dehydration of glycerol is not documented.

OBJECTIVES OF THE INVENTION

The primary objective of the invention is to provide a process for the preparation of the hydroxyacetone and 1,2 propylene glycol by glycerol.

Yet another objective of the present invention is to provide a process for the preparation of the hydroxyacetone by dehydration of glycerol.

Yet another objective of the present invention is to provide a process for the preparation of 1,2 propylene glycol by hydrogenation of glycerol.

Yet another objective of the present invention is to provide a process for the preparation that exhibits 80 to 100% selectivity towards the conversion of glycerol to hydroxyacetone or 1,2 propylene glycol in a one step process in the presence of a catalyst selected from Cu, Cr, Al, Ba, Mg, Zr, Zn, Si in combinations thereof.

SUMMARY OF THE INVENTION

Accordingly, the present invention relates to a catalytic process for the conversion of glycerol to hydroxyacetone or propylene glycol, with 80-100% selectivity, said process comprising the steps of, a) charging glycerol, a solvent and a pre-reduced catalyst into an autoclave with or without hydrogen in the mole ratio in the range of 15-500, b) flushing the reaction mixture as obtained in step (a) with nitrogen and subsequently heating the same in, the range of 180° C.-240° C. for a period of 1-24 hours with stirring speed in the range of 300-1700 rpm to get hydroxyacetone or propylene glycol and c) separating hydroxyacetone from reaction mixture as obtained in step (b) by fractional distillation to get pure hydroxyacetone, wherein the catalyst are selected from Cu, Cr, Al, Ba, Mg, Zr, Zn, Si or in combinations thereof in presence of a solvent.

In a preferred aspect, the process includes heating feedstock containing 10-80 wt % glycerol, more preferably 20-60 wt % glycerol with the metal catalyst in the temperature range of 180-220° C. at ambient nitrogen pressure. The solvents for the above process are selected from water, alcohols, and preferably aliphatic alcohols, alone or in combinations thereof.

Another aspect of the present invention, the catalyst composition of 20% $CuCr_2O_4$ with 80% of $SiO_2/Al_2O_3$/Zeolite support is used for selective conversion of glycerol to hydroxy acetone.

Yet another aspect, wherein the dehydration product, hydroxyacetone becomes a starting compound for hydrogenation to give selectively 1,2-propylene glycol.

In yet another aspect of the invention, the catalyst composition of 20% $CuCr_2O_4$ with 80% of $SiO_2/Al_2O_3$/Zeolite support for selective conversion of glycerol to 1,2 propylene glycol.

In another aspect of the present invention, wherein said nano structured Cu, Al, Cr catalysts have particle size in the range of 7-80 nm, more preferably between 7-50 nm.

DETAILED DESCRIPTION OF THE INVENTION

Figure 1:
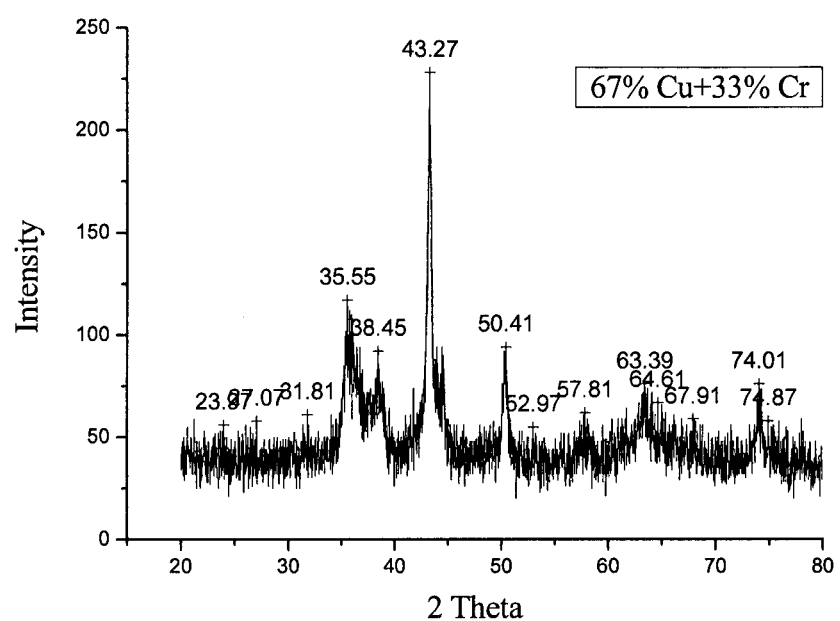
FIG. 1: XRD pattern of the 67% Cu, 33% Cr catalyst.

While the invention is susceptible to various modifications and alternative forms, specific aspect thereof has been shown by way of example and graphs and will be described in detail below. It should be understood, however that it is not intended to limit the invention to the particular forms disclosed, but on the contrary, the invention is to cover all modifications, equivalents, and alternative falling within the spirit and the scope of the invention as defined by the appended claims.

The Applicants would like to mention that the drawings are drawn to show only those specific details that are pertinent to understanding the aspects of the present invention so as not to obscure the disclosure with details that will be readily apparent to those of ordinary skill in the art having benefit of the description herein.

The terms "comprises", "comprising", or any other variations thereof, are intended to cover a non-exclusive inclusion, such that a process, catalyst composition that comprises a list of components does not include only those components but may include other components not expressly listed or inherent to such process. In other words, one or more elements in a system or process proceeded by "comprises . . . a" does not, without more constraints, preclude the existence of other elements or additional elements in the system or process.

In the following detailed description of the aspects of the invention, reference is made to the accompanying drawings and graphs that form part hereof and in which are shown by way of illustration specific aspects in which the invention may be practiced. The aspects are described in sufficient details to enable those skilled in the art to practice the invention, and it is to be understood that other aspects may be utilized and that charges may be made without departing from the scope of the present invention. The following description is, therefore, not to be taken in a limiting sense, and the scope of the present invention is defined only by the appended claims.

Accordingly, the present invention relates to a catalytic process for the conversion of glycerol to hydroxyacetone or propylene glycol, with 80-100% selectivity, said process comprising the steps of, a) charging glycerol, a solvent and a pre-reduced catalyst into an autoclave with or without hydrogen in the mole ratio in the range of 15-500, b) flushing the reaction mixture as obtained in step (a) with nitrogen and subsequently heating the same in the range of 180° C.-240° C., more preferably between 200-220° C. for a period of 1-24 hours, more preferably between 1-12 hours with stirring speed ranging from 300-1700 rpm, more preferably between 500-100 rpm, to get hydroxyacetone or propylene glycol, c) separating hydroxyacetone from reaction mixture as obtained in step (b) by fractional distillation to get pure hydroxyacetone.

One aspect of the present invention, wherein in step (a) the said catalysts are selected from the group Cu, Cr, Al, Ba, Zn, Si, Zr, Mg or in combinations thereof.

Another aspect of the present invention, wherein in step (a) the said solvents are selected from water, alcohols, preferably aliphatic alcohols, alone or in combinations thereof.

Yet another aspect of the present invention, wherein in step (a) said catalysts are optionally nano size.

Yet another aspect of the present invention, wherein in step (a) said catalysts are recyclable.

Yet another aspect of the present invention, where the catalyst composition having 50% Cu and Cr; 30% Al; 20% Zn in 2-propanol as solvent yields hydroxyacetone with 80 to 100% selectivity.

Yet another aspect of the present invention, where the catalyst composition of 13% Cu; 7% Cr; 80% $SiO_2$ in 2-propanol as solvent yields hydroxyacetone with 100% selectivity.

Yet another aspect of the present invention, where the nano sized catalyst composition of 50% Cu; 50% Al in water yields hydroxyacetone with 95 to 100% selectivity, wherein the catalyst having nano size in the range of 7 to 80 nm, preferably 7 to 13 nm.

Still another aspect of the present invention, where the catalytic process is carried out liquid phase.

Yet another aspect of the present invention, wherein said process is conducted in batch or continuous mode.

Yet another aspect of the present invention, wherein comprising a catalytic conversion of glycerol to 1,2, propylene glycol with 80-97% selectivity towards 1,2 propylene glycol, said catalyst selected from nano-structured Cu, Al, Cr and supported Cu—Cr and Pt, said process comprising: a) pressurizing a mixture of glycerol, a solvent and catalyst with $H_2$ with pressure in the range of 100 to 1500 psi, more preferably between 300-1000 psi b) heating the mixture of step (a) at temperature in the range of 180° C. to 250° C. for a period of 1-9 hours with stirring speed in the range of 300-1700 rpm, preferably 500-1000 rpm, in order to obtain 1,2-Propylene glycol.

Yet another aspect of the present invention, wherein said supports are selected from, but not limited to alumina, silica, zeolite and activated carbon.

Yet another aspect of the present invention, wherein said nano structured Cu, Al, Cr catalysts have particle size in the range of 7-80 nm.

Yet another aspect of the present invention, wherein concentration of glycerol used is in the range of 10 to 80%, more preferably between 20-60 wt %.

Yet another aspect of the present invention, wherein said process is conducted in batch or continuous mode.

Yet another aspect of the present invention, wherein said catalysts are recyclable.

Yet another aspect of the present invention, wherein the catalyst life achieved was 400 h for continuous conversion of glycerol to give hydroxyacetone and 1,2-PG.

Yet another aspect of the present invention, wherein comprising catalytic conversion of acetol to 1,2, propylene glycol with at least 50% selectivity towards 1,2 propylene glycol.

More particularly, the present invention, a one step process for the selective dehydration of glycerol to hydroxyacetone, with 80 to 100% selectivity towards hydroxyacetone, catalyzed by metals selected from Cu, Cr, Al, Ba, Zn, Si in combinations thereof, is disclosed. The solvents used for the process are selected from water, alcohols, and preferably aliphatic alcohols, alone or in combinations thereof. Dehydration of glycerol takes place at nitrogen ambient pressure and in the temperature range of 180-220° C.

The catalysts of the invention—in bulk form and as well as in nano sized form are prepared by known processes. The bulk catalysts are in the particle size range of 40-200μ and the nano catalysts have the particle size range of 5-100 nm.

The preparation of bulk Cu—Cr catalyst involves addition of ammonium chromate solution to a mixture of copper nitrate and aluminum nitrate dissolved in distilled water. Stirring is continued till a reddish brown precipitate was obtained. Other copper chromite catalysts of different compositions are also prepared by adding promoters such as, zinc, barium and aluminum, in the form of their nitrate salts. The resultant precipitate is filtered and dried in an oven at 110° C. The dried precipitate is then calcined in a muffle furnace for 1 h at 100° C. followed by 1 h at 200° C.; 1 h at 300° C.; and 2 h at 400° C. and activated under $H_2$ flow of 40-50 ml/min at 200° C. for 12 h.

The nano sized Cu—Al catalyst are prepared by adding a mixture of each of aqueous Cu $(NO_3)_2.3H_2O$ and Al $(NO_3)_3$ $9H_2O$ to aqueous $K_2CO_3$. The mixture is stirred simultaneously for 6 h at room temperature without using any template or a capping agent involving a simultaneous co-precipitation/digestion technique. After complete digestion, precipitated catalyst is filtered, washed and dried in static air oven at 100° C. for 8 h. The catalyst is further calcined at 400° C. and activated under H$_2$ flow of 40-50 ml/min at 1.4 MPa at 200° C. for 12 h.

The catalysts are recyclable as exemplified herein.

The process of the invention is conducted in batch or continuous mode. The recycling experiments of the inventive process are carried out in continuous mode.

The following examples are given to illustrate the process of the present invention and should not be construed to limit the scope of the present invention.

Example 1

Catalyst Preparation: Composition—50% Cu+Cr, 30% Al, 20% Zn

A mixture of 22.9 g of copper nitrate (0.095 moles of copper), 41.26 g of aluminum nitrate (0.110 moles of aluminum) and 23.5 g of zinc nitrate (0.079 moles of zinc) was dissolved in 200 ml of distilled water. A solution of ammonium chromate was prepared by dissolving 23.69 g of ammonium dichromate in 150 ml distilled water and adding drop wise approximately 22 ml of 30% aq. ammonia solution. The solution of nitrate was stirred while the ammonium chromate solution was poured into it in a thin stream. Stirring was continued till the addition was completed after which reddish brown precipitate was obtained. This precipitate was filtered and dried in oven at 110° C. for a period of 8 h. This dried precipitate was then calcined in a muffle furnace.
Calcination Program:
1 h at 100° C.
1 h at 200° C.
1 h at 300° C.
2 h at 400° C.
Activation Program: 12 h at 473 K under H$_2$ flow of 42.5 ml/min
Characterization
1. Surface area—51.58 m$^2$/g,
2. NH$_3$ Temperature Programming Desorption (TPD)—0.985 mmol/g Example 2

Catalyst Preparation: Composition—71% Cu+Cr, 19% Al, 10% Ba

A mixture of 40.25 g of copper nitrate (0.168 moles of copper), 30.98 g of aluminum nitrate (0.082 moles of aluminum) and 10.44 g of barium nitrate (0.041 moles of barium) was dissolved in 405 ml of distilled water. A solution of ammonium chromate (0.129 moles of chromium) was prepared by dissolving 32.7 g of ammonium dichromate in 158 ml distilled water and adding drop wise approximately 25 ml of 30% aq. ammonia solution. The solution of nitrate was stirred while the ammonium chromate solution was poured into it in a thin stream. Stirring was continued till the addition was completed after which reddish brown precipitate was obtained. This precipitate was filtered and dried in oven at 110° C. This dried precipitate was then calcined in a muffle furnace following the programme as specified here under.
Calcination Program:
1 h at 100° C.
1 h at 200° C.
1 h at 300° C.
2 h at 400° C.

The calcined catalyst was activated for 12 h at 200° C. under H$_2$ flow of 48 ml/min and characterized for surface area and NH$_3$ TPD.
Characterization
1. Surface area—54.67 m$^2$/g,
2. NH$_3$ TPD—0.1538 mmol/g Example 3

Catalyst Preparation: Composition—67% Cu, 33% Cr 50 g of copper nitrate (0.2069 moles of copper) was dissolved in 165 ml of distilled water. A solution of ammonium chromate (0.1039 moles of Cr) was prepared by dissolving 26.18 g of ammonium dichromate in 123 ml distilled water and adding drop wise approximately 18.158 ml of 30% aq. ammonia solution. The solution of nitrate was stirred while the ammonium chromate solution was poured into it in a thin stream. Stirring was continued till the addition was completed after which reddish brown precipitate was obtained. This precipitate was filtered and dried in oven at 110° C. This dried precipitate was then calcined in a muffle furnace following the programme as specified here under.
Calcination Program:
1 h at 100° C.
1 h at 200° C.
1 h at 300° C.
2 h at 400° C.
The calcined catalyst was activated for 12 h at 200° C. under H$_2$ flow of 43 ml/min and characterized for surface area and NH$_3$ TPD.
Characterization
1. Surface area—47.63 m$^2$/g,
2. NH$_3$ TPD—0.3414 mmol/g
3. XRD pattern of the prepared and activated Cu—Cr catalyst in FIG. 1 shows the peaks at 2θ values of 35.55° and 74.01° corresponding to mixed phases of Cu$^{2+}$ and Cr$^{3+}$ along with the peaks at 2θ values of 43.27° and 50.4° assigned to metallic copper. The presence of both copper and chromium in the XRD pattern confirms the Cu—Cr catalyst formation.
4.

TABLE 1

| EDX analysis showing elemental composition of the activated 50% Cu + Cr, 30% Al, 20% Zn. | |
|---|---|
| Elements | At % |
| Cu | 28 |
| Cr | 25 |
| Al | 29 |
| Zn | 18 |

Example 4

Catalyst Preparation: Composition—50% Cu, 50% Al (Nano Size 7-11 nm)

Nanostructured Cu:Al catalyst was prepared by simultaneous addition of a mixture of 0.05M each aqueous Cu (NO$_3$)$_2$.3H$_2$O, Al (NO$_3$)$_3$9H$_2$O and 0.2M aqueous K$_2$CO$_3$ (6.91 g) into 250 ml of distilled water. This mixture was stirred simultaneously for 6 h at 30° C. without using any template or a capping agent involving a simultaneous coprecipitation/digestion technique. After complete digestion, precipitated catalyst was filtered, washed and dried in static air oven at 100° C. for 8 h. The catalyst was calcined at 400° C. and activated under $H_2$ flow of 44.5 ml/min at 1.4 MPa at 200° C. for 12 h.

Figure 2:
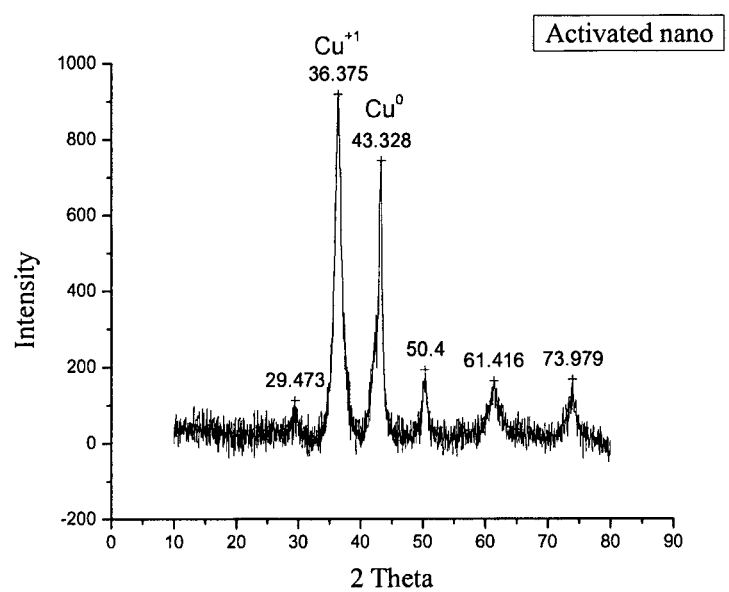
FIG. 2: XRD pattern of nano 50% Cu, 50% Al catalyst
Figure 3:
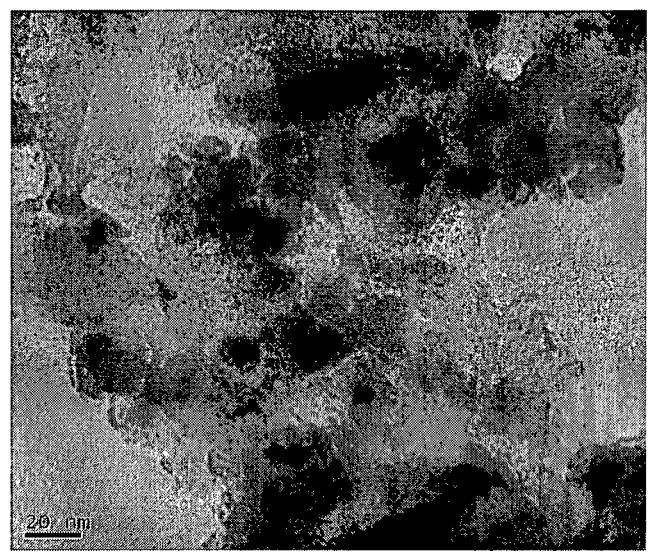
FIG. 3: TEM image of nano 50% Cu, 50% Al catalyst

Characterization:
1. Surface area—31.36 m$^2$/g,
2. $NH_3$ TPD—0.4513 mmol/g
3. XRD pattern of the activated 50% Cu and 50% Al nano catalyst in FIG. 2 showed two broad diffraction peaks at 2θ values of 36.54° and 43.36° which could be assigned to $Cu^+$ and metallic Cu respectively. By using Scherrer equation, crystallite size obtained was 7 nm confirming that the prepared catalyst was a nano catalyst.
4. The particle size of the nano catalyst estimated was 7-11 nm from the TEM image of the catalyst as shown in FIG. 3. This also confirms that the catalyst is a nano catalyst.
5.

TABLE 2

EDX analysis showing elemental composition of activated nano Cu (50%):Al (50%) catalyst.

| Elements | At % |
|---|---|
| Cu | 55 |
| Al | 45 |

Example 5

Catalyst Preparation: Composition—70% Cu, 30% Al (Nano Size 7-12 nm)

12.74 g of copper nitrate (0.0527 moles of copper) and 8.37 g of aluminium nitrate (0.0223 moles of aluminium) was dissolved in 250 ml of distilled water. A solution of 0.7023 M $K_2CO_3$ was prepared by dissolving 24.26 g of $K_2CO_3$ into 250 ml of distilled water. The solution of nitrate and $K_2CO_3$ was added simultaneously through separating funnel at 25-30° C. After the complete precipitation allow the system to digest under same condition for 6 h at 25-30° C. This precipitate was filtered and dried in oven at 100° C. for 8 h. This dried precipitate was then calcined in a muffle furnace for 4 h at 400° C. and activated for 12 h at 200° C. under $H_2$ flow of 44.5 ml/min.

Characterization:
1. Surface area—31.36 m$^2$/g,
2. $NH_3$ TPD—0.2359 mmol/g
3. The particle size of the nano catalyst estimated was 7-12 nm from the TEM image of the catalyst

Example 6

Catalyst Preparation: Composition—20% Cu/C

The 20% Cu/C catalyst was prepared by impregnation method. A solution of Cu $(NO_3)_2 \cdot 3H_2O$ (7.6046 g in 10 mL of water) was added to the hot slurry of carbon (8 g) made in water with stirring. This mixture was stirred for the 6 h. After 6 h to this solution 10% ammonium carbonate solution was added with constant stirring till the pH reaches to 9. The resulting slurry was filtered to obtain a solid cake and dried in oven at 100° C. for 6 h. This dried precipitate was then calcined in a muffle furnace for 10 h at 500° C. and activated for 12 h at 300° C. under $H_2$ flow of 40 ml/min.

Characterization:
1. Surface area—20% Cu/C—700 m$^2$/g

Example 7

Catalyst Preparation: Composition—20% $CuCr_2O_4$ on $SiO_2$, $Al_2O_3$ and H-β zeolite A weighed quantity of copper nitrate corresponding to 0.2069 moles of copper was dissolved in 165 ml of distilled water. A solution of ammonium chromate corresponding to 0.1039 moles of Cr was prepared in 123 ml distilled water and adding drop wise approximately 18.158 ml of 30% aq. ammonia solution. The solution of nitrate was stirred while the ammonium chromate solution was poured into it in a thin stream. Stirring was continued till the addition was completed after which reddish brown precipitate was obtained. Simultaneously, weighed quantity of the respective supports corresponding to 20 wt % of Cu—Cr catalysts was added to the above solution under stirring and the stirring was continued for 6 h. The supported catalyst in the form of a solid was filtered and dried in oven at 110° C. This dried catalyst was then calcined in a muffle furnace following the programme as specified here under.

Calcination Program:
1 h at 100° C.
1 h at 200° C.
1 h at 300° C.
2 h at 400° C.

The calcined catalyst was activated for 12 h at 200° C. under $H_2$ flow of 43 ml/min and characterized for surface area.

Figure 4:
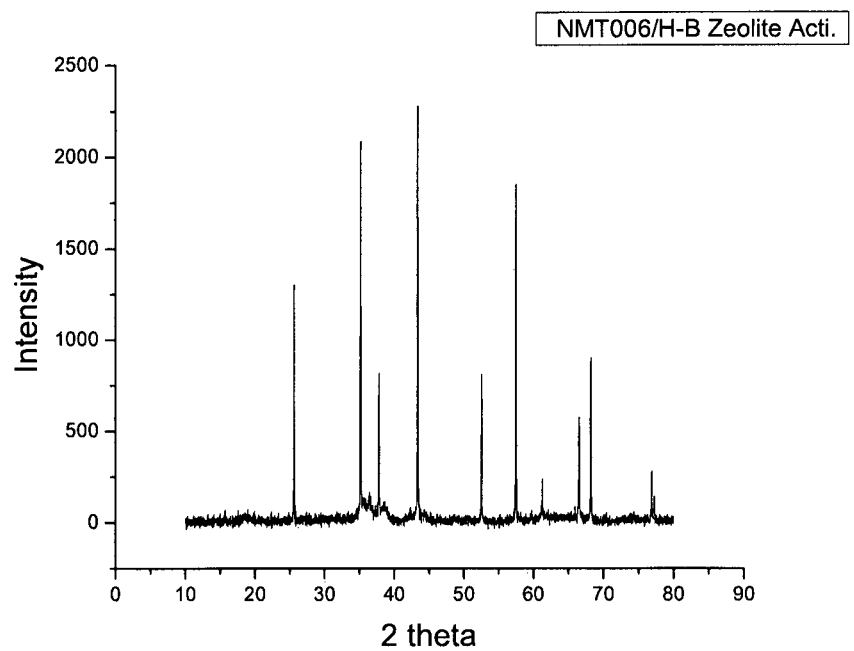
FIG. 4: XRD pattern of 20% $CuCr_2O_4$/H-β zeolite catalyst

Characterization:
1. Surface area—a. $CuCr_2O_4/Al_2O_3$—377.35 m$^2$/g,
   b. $CuCr_2O_4/SiO_2$—168.50 m$^2$/g,
   c. CuCr2O4/H-β zeolite—180 m$^2$/g.
2. XRD pattern of the prepared and activated 20% $CuCr_2O_4$/H-β zeolite catalyst shown in FIG. 4 shows the peaks at 2θ values of 34.55° and 70.01° corresponding to mixed phases of $Cu^{2+}$ and $Cr^{3+}$ along with the peaks at 2θ values of 43.27° assigned to metallic copper. The presence of both copper and chromium in the XRD pattern confirms the supported Cu—Cr catalyst formation.

Examples of Dehydration of Glycerol

Example 8

20 wt % glycerol was dehydrated at nitrogen ambient pressure at 220° C. using 80 g of 2-propanol as solvent. 0.01 g/ml of 67% Cu and 33% Cr catalyzed the reaction for 5 h to give glycerol conversion of 37% with 86% selectivity to hydroxyacetone, 10% 1,2-propylene glycol, 4% ethylene glycol and <0.01% to other products.

Example 9

20 wt % glycerol was dehydrated at nitrogen ambient pressure at 220° C. using 80 g of 2-propanol as solvent. 0.01 g/ml of 50% Cu+Cr; 30% Al; 20% Zn catalyzed the reaction for 5 h to give glycerol conversion of 32% with 100% selectivity to hydroxyacetone.

Example 10

20 wt % glycerol was dehydrated at nitrogen ambient pressure at 220° C. using 80 g of 2-propanol as solvent. 0.01 g/ml of 71% Cu+Cr; 19% Al; 10% Ba catalyzed the reaction for 3 h to give glycerol conversion of 34% with 90% selectivity to hydroxyacetone, 8% 1,2-propylene glycol, <2% ethylene glycol and <0.01% to other products.

Example 11

20 wt % glycerol was dehydrated at nitrogen ambient pressure at 220° C. using 80 g of 2-propanol as solvent. 0.01 g/ml of 13% Cu+7% Cr+80% $SiO_2$ catalyzed the reaction for 3 h to give glycerol conversion of 8% with 100% selectivity to hydroxyacetone, <0.01% 1,2-propylene glycol, <0.01% ethylene glycol and <0.01% to other products.

Example 12

20 wt % glycerol was dehydrated at nitrogen ambient pressure at 220° C. using 80 g of water as solvent. 0.8 g of 50% Cu+50% Al catalyst of nano size catalyzed the reaction to give glycerol conversion of 17% with 100% selectivity to hydroxyacetone.

Example 13

20 wt % glycerol was dehydrated at nitrogen ambient pressure at 220° C. using 80 g of water as solvent. 0.8 g of 70% Cu+30% Al catalyst of nano size catalyzed the reaction to give glycerol conversion of 23% with 89% selectivity to hydroxyacetone and 11% to 1,2-proplylene glycol.

Example 14

20 wt % glycerol was dehydrated at nitrogen ambient pressure at 220° C. using 80 g of water as solvent. 1 g of 50% Cu+50% Mg catalyst of nano size catalyzed the reaction to give glycerol conversion of 24% with 79% selectivity to hydroxyacetone, 20% to 1,2-propylene glycol and 1% to ethylene glycol.

Example 15

20 wt % glycerol was dehydrated at nitrogen ambient pressure at 220° C. using 80 g of water as solvent. 1 g of 50% Cu+50% Zr catalyst of nano size catalyzed the reaction to give glycerol conversion of 20% with 87% selectivity to hydroxyacetone and 13% to 1,2-propylene glycol.

Example 16

30 wt % glycerol was dehydrated in nitrogen ambient pressure at 220° C. using 70 g of water as solvent. 0.01 g/ml of 50% Cu+50% Al catalyst of nano size catalyzed the reaction for 3 h to give glycerol conversion of 23% with 91% selectivity to hydroxyacetone, 8% to 1,2-proplylene glycol and 1% to ethylene glycol.

Example 17

60 wt % glycerol was dehydrated in nitrogen ambient pressure at 220° C. using 40 g of water as solvent. 0.01 g/ml of 50% Cu+50% Al catalyst of nano size catalyzed the reaction for 3 h to give glycerol conversion of 17% with 92% selectivity to hydroxyacetone, 7% to 1,2-proplylene glycol and 1% to ethylene glycol.

Example 18

Dehydration of 80 wt % glycerol followed by acetol hydrogenation in a single step at 220° C. in 20 g of water as a solvent using 0.01 g/ml of 67% Cu+33% Cr catalyst in 5 h gave 21% conversion of glycerol with selectivity's of 69% to 1,2-propylene glycol and 31% to hydroxyacetone.

Example 19

20 wt % glycerol was dehydrated in nitrogen ambient pressure at 220° C. using 80 g of water as solvent. 0.8 g of 50% Cu+50% Al catalyst of nano size catalyzed the reaction to yield 21% conversion of glycerol in 7 h with 95% selectivity to hydroxyacetone and 5% selectivity to 1,2-proplylene glycol.

Example 20

Continuous dehydration of 20 wt % glycerol in 80 g of water was carried out at reaction conditions of 220° C., 20 g of 50% Cu+50% Al catalyst of nano size, 2 MPa $N_2$ pressure at GHSV, 513 $h^{-1}$, and LHSV, 1.53 $h^{-1}$. The liquid analysis after every 5 h showed that the conversion of glycerol was ≤95% with 50-54% selectivity to acetol and 30-35% to 1,2-PG.

Our catalyst showed the stability up to 400 h for continuous dehydration of glycerol in which 1,2-PG was also a major product.

Example 21

In order to establish reusability of catalyst for glycerol hydrogenolysis reaction, the catalyst was filtered after reaction and washed with a solvent. Then it was dried in oven at 383K and regenerated by reducing under hydrogen (45 ml/min) and used for the subsequent reactions. This procedure was followed for two subsequent hydrogenolysis reactions and results are shown in Table 3. As can be seen from Table 3 the activities of bulk catalysts decreased substantially while the nano catalyst showed considerable activity even after the second recycle in terms of turn over frequency (TOF) expressed as $h^{-1}$.

TABLE 3

CATALYST RECYCLES EXPERIMENTS
Reaction Conditions: Temp.- 220° C., 20 wt % Glycerol, Solvent- 2-Propanol, Catalyst- 0.01 g/ml, Reaction time- 5 h.

| Catalyst | | TOF/$h^{-1}$ | Selectivity | | | |
| --- | --- | --- | --- | --- | --- | --- |
| | | | 1,2 PG | Acetol | ETG | Others |
| Nano | (Fresh) | 2.96 | 88 | 7 | 5 | <0.01 |
| catalyst | (Used I) | 2.58 | 78 | 18 | 4 | <0.01 |
| Cu:Al (1:1) | (Used II) | 2.27 | 71 | 24 | 5 | <0.01 |
| Bulk catalyst | (Fresh) | 0.92 | 74 | 24 | 2 | <0.01 |
| (Cu:Cr) | (Used I) | 0.69 | 68 | 30 | 2 | <0.01 |
| | (Used II) | 0.61 | 65 | 32 | 3 | <0.01 |
| literature | (Fresh) | 1.26 | 63 | 32 | 5 | <0.01 |
| catalyst | (Used I) | 1.09 | 55 | 41 | 4 | <0.01 |
| (Cu:Cr) | (Used II) | 0.84 | 51 | 43 | 6 | <0.01 |

Example 22

Separation of Acetol from the Reaction Mixture

Separation of acetol from reaction mixture was carried out by fractional distillation under vacuum. Boiling point of glycerol is 290° C. which is higher than that of acetol i.e. 145° C. Due to the large difference in boiling points of glycerol and acetol, acetol is easily separated from the reaction mixture as the first fraction and residue contains unreacted glycerol.

Example 23

Experimental Setup

I. Batch Process:

Glycerol hydrogenolysis reactions were carried in a 300 ml capacity autoclave (Parr Instruments Co., USA) which was equipped with stirrer, heater, automatic temperature controller and a sample port for liquid sampling. The required quantity of diluted glycerol and pre-reduced catalyst were introduced into the autoclave. The contents were first flushed with nitrogen and then with hydrogen. Then the reactor was heated to the reaction temperature 220° C. and the system was pressurized with 750 psi $H_2$ pressure. The reaction was started by stirring the reactor content at 1000 rpm throughout the reaction.

Glycerol dehydration was also carried out by same experimental procedure at $N_2$ ambient atmosphere without $H_2$ pressure.

II. Continuous Process:

Continuous reaction was carried out in a fixed bed reactor equipped with a single tube SS reactor of 40 ml capacity, high pressure liquid feed pump, mass flow controllers, gas sensor, gas flow meter and condenser. The glycerol solution and hydrogen gas were introduced co-currently down flow over the catalyst bed through the reactor at the desired gas and liquid flow rates. The downstream of the reactor was first passed through a gas-liquid separator and then through the condenser in order to separate the excess hydrogen gas and to collect the reaction product crude for the periodic analysis.

Examples of Supported Catalysts for the Hydrogenolysis of Glycerol

Example 24

20 wt % glycerol was hydrogenated at 750 psi hydrogen pressure at 220° C. using 80 g of 2-propanol as solvent. 0.01 g/ml of copper and chromium (67% Cu+33% Cr) catalyzed the reaction for 5 h to yield 16% conversion of glycerol with analysis as follows: 91% 1,2-propylene glycol, 8% acetol, 1% ethylene glycol and <0.01% other products.

Example 25

20 wt % glycerol was hydrogenated at 1000 psi hydrogen pressure and 220° C. using 80 g of 2-propanol as a solvent. 0.01 g/ml catalyst of 20% $CuCr_2O_4/SiO_2$ catalyze the reaction for 5 h to give glycerol conversion of 20% with 97% selectivity to 1,2-PG, 2% to acetol and 1% to ethylene glycol (EG).

Example 26

20 wt % glycerol was hydrogenated at 500 psi hydrogen pressure and 220° C. using 80 g of water as a solvent. 0.01 g/ml catalyst of 20% $CuCr_2O_4/Al_2O_3$ catalyze the reaction for 5 h to give glycerol conversion of 13% with 45% selectivity to 1,2-PG, 55% to acetol.

Example 27

20 wt % glycerol was hydrogenated at 500 psi hydrogen pressure and 220° C. using 80 g of 2-propanol as a solvent. 0.01 g/ml catalyst of 20% $CuCr_2O_4$/H-β zeolite catalyze the reaction for 5 hours to give glycerol conversion of 33% with 96% selectivity to 1,2-PG and 4% to acetol.

Example 28

55 wt % glycerol was hydrogenated at 500 psi hydrogen pressure and 220° C. using 45 g of water as a solvent. Activated 0.01 g/ml catalyst of 20% Cu/C catalyze the reaction for 5 h to give glycerol conversion of 20% with 46% selectivity to 1,2-PG and 54% selectivity to acetol.

Example 29

20 wt % glycerol was hydrogenated at 500 psi hydrogen pressure at 220° C. using 80 g of water as solvent. 0.01 g/ml catalyst of 3% Pt/C catalyzed the reaction in 5 h to give glycerol conversion of 32% with 91% selectivity to 1,2-propylene glycol, 2% to acetol and 7% ethylene glycol and <0.01% other products.

Examples of Acetol Hydrogenation to 1,2-PG

Example 30

20 wt % acetol was hydrogenated at 300 psi hydrogen pressure and 220° C. using 80 g of 2-propanol as a solvent. 0.01 g/ml catalyst of 67% Cu+33% Cr catalyze the reaction for 5 h to give acetol conversion of 97% with 78% selectivity to 1,2-PG, and 22% to others.

Example 31

20 wt % acetol was hydrogenated at 1000 psi hydrogen pressure and 220° C. using 80 g of 2-propanol as a solvent. 0.01 g/ml catalyst of 67% Cu+33% Cr catalyze the reaction for 5 h to give acetol conversion of 97% with 92% selectivity to 1,2-PG, 0.5% EG and 7.5% to other products.

Example 32

20 wt % acetol was hydrogenated at 1000 psi hydrogen pressure and 220° C. using 80 g of water as a solvent. 0.008 g/ml catalyst of 50% Cu+50% Al catalyze the reaction for 5 h to give acetol conversion of 75% with 52% selectivity to 1,2-PG and 48% to other products.

Example 33

20 wt % acetol obtained from example 13 was hydrogenated at 1000 psi hydrogen pressure and 220° C. using 80 g of water as a solvent. 0.01 g/ml catalyst of 50% Cu+50% Al catalyze the reaction for 5 h to give acetol conversion of 95% with 93% selectivity to 1,2-PG.

ADVANTAGES OF THE PRESENT INVENTION

Improved process for the preparation of hydroxyacetone or PG by dehydration of glycerol with 100% selectivity to hydroxyacetone.

Single step process for the production of hydroxyacetone or PG via glycerol.

Minimize formation of side products in glycerol hydrogenolysis, such as ethylene glycol, propanol.

Nano catalysts showed very high performance in this invention and were prepared by simple co-precipitation and digestion method without using any template and/or capping agent.

Mild reaction conditions (ambient pressure for dehydration).

Catalysts reusability.

Formation of 1,2-PG under dehydration conditions, without adding hydrogen. This is due to the in-situ generation of hydrogen by glycerol reforming reaction.

The catalyst life achieved was 400 h for the continuous operation which produces both hydroxyacetone and 1,2-PG, under dehydration conditions.

The advantages of the disclosed invention are thus attained in an economical, practical, and facile manner. While preferred aspects and example configurations have been shown and described, it is to be understood that various further modifications and additional configurations will be apparent to those skilled in the art. It is intended that the specific embodiments and configurations herein disclosed are illustrative of the preferred nature and best mode of practicing the invention, and should not be interpreted as limitations on the scope of the invention.

We claim:

1. A catalytic process for the conversion of glycerol to hydroxyacetone, with 80-100% selectivity, said process comprising the steps of,
   a. charging glycerol, a solvent and a pre-reduced catalyst into an autoclave in the mole ratio in the range of 15-500,
   b. flushing the reaction mixture as obtained in step (a) with nitrogen and subsequently heating the same in the range of 180° C.-240° C. for a period of 1-24 hours with stirring speed in the range of 300-1700 rpm to get hydroxyacetone or propylene glycol;
   (c) separating hydroxyacetone from reaction mixture as obtained in step (b) by fractional distillation to get pure hydroxyacetone.

2. The process as claimed in claim 1, wherein in step (a) the said catalysts are selected from the group Cu, Cr, Al, Ba, Zn, Si, Zr, Mg or in combinations thereof.

3. The process as claimed in claim 1, wherein in step (a) the said solvents are selected from water, alcohols, preferably alone or in combinations thereof.

4. The process as claimed in claim 1 or 2, wherein in step (a) said catalysts are optionally nano size.

5. The process as claimed in claim 1 or 2, wherein in step (a) said catalysts are recyclable.

6. The process as claimed in claim 1 or 2, where the catalyst composition having 50 mole % Cu and Cr; 30% mole Al; 20 mole % Zn in 2-propanol as solvent yields hydroxyacetone with 80 to 100% selectivity.

7. The process as claimed in claim 1 or 2, where the catalyst composition of 13 mole % Cu; 7 mole % Cr; 80 mole % $SiO_2$ in 2-propanol as solvent yields hydroxyacetone with 100% selectivity.

8. The process as claimed in claim 1 or 2, where the nano sized catalyst composition of 50 mole % Cu; 50 mole % Al in water yields hydroxyacetone with 95 to 100% selectivity, wherein the catalyst having nano size in the range of 7 to 80 nm.

9. The process as claimed in claim 1, where the catalytic process is carried out in liquid phase.

10. The process as claimed in claim 1, wherein said process is conducted in batch or continuous mode.

11. The process as claimed in claim 1, wherein catalyst life achieved is 400 hour for continuous conversion of glycerol to hydroxyacetone.

12. A process for the catalytic conversion of glycerol to 1,2, propylene glycol with 80-97% selectivity towards 1,2 propylene glycol, said catalyst selected from nano-structured Cu, Al, Cr and supported Cu—Cr and Pt, said process comprising:
   a. pressurizing a mixture of glycerol, a solvent and catalyst with $H_2$ in the range of 6.8 to 100 bar;
   b. heating the mixture of step (a) at temperature ranging between 180° C. to 250° C. for a period in the range of 1-9 hours with stirring speed in the range of 300-1700 rpm, in order to obtain 1,2-Propylene glycol.

13. The process as claimed in claim 12, wherein said supports are selected from, but not limited to alumina, silica, zeolite and activated carbon.

14. The process as claimed in claim 12, wherein said nano structured Cu, Al, Cr catalysts have particle size in the range of 7-80 nm.

15. The process as claimed in claim 12, wherein concentration of glycerol used is in the range of 20 to 60 wt %.

16. The process as claimed in claim 1, wherein said process is conducted in batch or continuous mode.

17. The process as claimed in claim 12, wherein said catalysts are recyclable.

18. The process as claimed in claim 12, wherein the catalyst life achieved is 400 hour for continuous conversion of glycerol to give 1,2-propylene glycol.

19. The process as claimed in claim 1, further comprising catalytic conversion of acetol to 1,2, propylene glycol with at least 50% selectivity towards 1,2 propylene glycol.

20. The process as claimed in claim 3, wherein the alcohols are aliphatic alcohols.

21. The process of claim 8, wherein the catalyst having nano size in the range of 7 to 13 nm.

* * * * *